(12) United States Patent
Liu et al.

(10) Patent No.: US 10,568,765 B2
(45) Date of Patent: *Feb. 25, 2020

(54) OPHTHALMIC DOCKING SYSTEM WITH 3-DIMENSIONAL AUTOMATIC POSITIONING USING MAGNETIC SENSING ARRAY

(71) Applicant: AMO DEVELOPMENT, LLC, Santa Ana, CA (US)

(72) Inventors: Harvey I. Liu, Fremont, CA (US); John P. Beale, San Jose, CA (US)

(73) Assignee: AMO DEVELOPMENT, LLC, Santa Ana, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 15/786,484

(22) Filed: Oct. 17, 2017

(65) Prior Publication Data

US 2019/0110923 A1 Apr. 18, 2019

(51) Int. Cl.
*A61F 9/009* (2006.01)
*A61B 3/10* (2006.01)
(Continued)

(52) U.S. Cl.
CPC .............. *A61F 9/009* (2013.01); *A61B 3/102* (2013.01); *A61B 18/18* (2013.01); *A61B 90/20* (2016.02);
(Continued)

(58) Field of Classification Search
CPC ................................................ A61B 2005/105
See application file for complete search history.

(56) References Cited

U.S. PATENT DOCUMENTS 4,629,989 A * 12/1986 Riehl ................... A61B 5/0555
324/300
5,463,669 A * 10/1995 Kaplan .................... A61B 6/08
378/170
(Continued)

FOREIGN PATENT DOCUMENTS

| EP | 2913036 A1 | 9/2015 |
|---|---|---|
| WO | 2007022993 A2 | 3/2007 |
| WO | 2007087208 A2 | 8/2007 |

OTHER PUBLICATIONS

Fulda et al. "Alignment sensing for optical cavities using radio-frequency jitter modulation" Applied Optics vol. 56, No. 13/ May 1, 2017 (pdf attached) (Year: 2017).*
(Continued)

*Primary Examiner* — Michael W Kahelin
*Assistant Examiner* — Shirley X Jian
(74) *Attorney, Agent, or Firm* — Johnson & Johnson Surgical Vision, Inc.

(57) ABSTRACT

A magnetic positioning system and related method for automated or assisted eye-docking in ophthalmic surgery. The system includes a magnetic field sensing system on a laser head and a magnet on a patient interface to be mounted on the patient's eye. The magnetic field sensing system includes four magnetic field sensors located on a horizontal plane for detecting the magnetic field of the magnet, where one pair of sensors are located along the X direction at equal distances from the optical axis of the laser head and another pair are located along the Y direction at equal distances from the optical axis. Based on relative magnitudes of the magnetic field detected by each pair of sensors, the magnetic field sensing system determines whether the patient interface
(Continued)

is centered on the optical axis. The system controls the laser head to move toward the patient interface until the latter is centered on the optical axis.

15 Claims, 2 Drawing Sheets

(51) Int. Cl.
    *A61B 18/18*     (2006.01)
    *A61F 9/008*     (2006.01)
    *A61F 9/007*     (2006.01)
    *A61B 90/20*     (2016.01)
    *A61B 90/90*     (2016.01)
    *A61B 34/20*     (2016.01)
    *A61B 90/00*     (2016.01)

(52) U.S. Cl.
    CPC .............. *A61B 90/90* (2016.02); *A61F 9/008* (2013.01); *A61F 9/0079* (2013.01); *A61B 2034/2051* (2016.02); *A61B 2090/0811* (2016.02); *A61F 2009/00844* (2013.01); *A61F 2009/00855* (2013.01); *A61F 2009/00872* (2013.01)

(56) References Cited

U.S. PATENT DOCUMENTS

| | | | |
|---|---|---|---|
| 5,872,086 A | 2/1999 | Ellis et al. | |
| 6,758,845 B1* | 7/2004 | Weckwerth | A61B 18/203 606/9 |
| 6,927,860 B2* | 8/2005 | Podoleanu | A61B 3/102 356/479 |
| 7,390,089 B2* | 6/2008 | Loesel | A61F 9/008 351/208 |
| 7,817,908 B2* | 10/2010 | Kawai | G02B 27/646 348/208.11 |
| 7,866,829 B2* | 1/2011 | Takeuchi | G03B 9/02 353/88 |
| 8,192,346 B2* | 6/2012 | Kawano | A61B 1/00158 600/9 |
| 8,248,204 B2* | 8/2012 | Takeshima | G01V 15/00 340/10.1 |
| 8,378,967 B2* | 2/2013 | Noda | G06F 3/038 178/18.07 |
| 8,821,015 B2* | 9/2014 | Stagnitto | A61B 6/4291 378/205 |
| 8,863,749 B2* | 10/2014 | Gooding | A61F 9/00827 128/898 |
| 9,044,304 B2* | 6/2015 | Raksi | A61F 9/009 |
| 9,089,401 B2 | 7/2015 | Raksi et al. | |
| 9,103,916 B2* | 8/2015 | Waters | G01S 19/48 |
| 9,141,194 B1* | 9/2015 | Keyes | G06F 3/017 |
| 9,237,967 B2* | 1/2016 | Gooding | A61B 3/102 |
| 9,336,477 B2* | 5/2016 | Nitta | G06K 19/07762 |
| 9,351,879 B2 | 5/2016 | Gooding et al. | |
| 9,358,157 B2* | 6/2016 | Rathjen | A61F 9/00825 |
| 9,615,972 B2* | 4/2017 | Shibata | A61F 9/00825 |
| 9,679,235 B2* | 6/2017 | Sugar | G06K 19/0702 |
| 9,704,003 B1* | 7/2017 | Anderson | G06K 7/10366 |
| 9,795,509 B2* | 10/2017 | Heitel | A61F 9/009 |
| 9,841,507 B2* | 12/2017 | Waters | G01S 19/48 |
| 9,874,641 B2* | 1/2018 | Waters | G01S 19/48 |
| 10,043,125 B2* | 8/2018 | Park | G06K 19/07762 |
| 10,117,740 B1* | 11/2018 | Lee | A61F 2/1624 |
| 2006/0280360 A1* | 12/2006 | Holub | G01J 3/02 382/162 |
| 2008/0297291 A1* | 12/2008 | Kawano | A61B 1/00158 335/285 |
| 2009/0234335 A1* | 9/2009 | Yee | A61F 9/00829 606/5 |
| 2010/0188216 A1* | 7/2010 | Nielsen | G01V 3/081 340/540 |
| 2010/0220054 A1* | 9/2010 | Noda | G06F 3/014 345/156 |
| 2010/0253476 A1* | 10/2010 | Poutiatine | A61J 7/0053 340/10.1 |
| 2011/0017222 A1* | 1/2011 | Li | A61N 2/06 128/899 |
| 2012/0172126 A1* | 7/2012 | Padovani | G06F 3/011 463/36 |
| 2012/0230473 A1* | 9/2012 | Stagnitto | A61B 6/4291 378/205 |
| 2013/0165911 A1 | 6/2013 | Raksi et al. | |
| 2013/0226160 A1* | 8/2013 | Rathjen | A61F 9/00825 606/4 |
| 2013/0293416 A1* | 11/2013 | Waters | G01S 19/48 342/357.31 |
| 2014/0276673 A1 | 9/2014 | Heitel et al. | |
| 2015/0106373 A1* | 4/2015 | Haverinen | G06F 16/285 707/737 |
| 2015/0206044 A1* | 7/2015 | Nitta | G06K 19/07762 235/492 |
| 2016/0292563 A1* | 10/2016 | Park | G06K 19/07762 |

OTHER PUBLICATIONS

Hae et al. "Using RFID for Accurate Positioning" Journal of Global Positioning Systems 2004 vol. 3, No. 1-2:32-39 (pdf attached) (Year: 2017).*
International Search Report and Written Opinion for Application No. PCT/IB2018/058020, dated Jan. 3, 2019, 13 pages.

* cited by examiner

OPHTHALMIC DOCKING SYSTEM WITH 3-DIMENSIONAL AUTOMATIC POSITIONING USING MAGNETIC SENSING ARRAY

BACKGROUND OF THE INVENTION

Field of the Invention

This invention relates to docking of an instrument head to a patient interface device during laser ophthalmic surgery, and in particular, it relates to devices, system and method that aid automatic docking based on automatic positioning using a magnetic sensing system on the instrument head and the patient interface device.

Description of Related Art

Significant developments in laser technology have led to its application in the field of ophthalmic surgery, and laser surgery has become the technique of choice for ophthalmic surgical applications. Ophthalmic surgery is a precision operation and requires precise coupling between the surgical tool (i.e., the laser beam) and the region to be surgically altered (i.e., a portion of the patient's eye). Movement of the eye with respect to the intended focal point of the laser beam can lead to non-optimal results and could even result in permanent damage to tissue within the eye. Given that eye movement is often the result of autonomic reflex, techniques have been developed in an attempt to stabilize the position of a patient's eye with respect to an incident laser beam.

Mechanical stabilization devices, referred to as patient interfaces (PI), have been developed for coupling the patient's eye to the laser system. A PI typically has a component that directly contacts the eye, and engages and stabilizes the eye; meanwhile, the PI is attached to the laser system, so that the laser beam can be aligned to the eye. Currently available designs of PIs typically have either a single-piece or a two-piece structure.

Using a two-piece structure, the surgeon installs a lens cone on the beam delivery head of the laser system, and installs a suction ring assembly on the patient's eye using a suction force, and then docks the two pieces (lens cone and suction ring assembly) together using the motorized gantry of the laser system. In a single-piece structure, the lens cone and the suction ring assembly are integrated as one piece. In some systems that use a single-piece PI, the surgeon first installs the PI on the patient's eye, and then brings the laser head to the vicinity of the PI using the motorized gantry, and docks the laser head with the PI. A single-piece PI, or the piece of a two-piece PI that contacts the eye, is typically a single-use item intended to be used only once.

SUMMARY

Embodiments of the present invention provide a magnetic positioning system and related method for automated or assisted eye-docking in ophthalmic surgery. The system includes a magnetic field sensing system provided on the laser head and one or more magnets provided on the PI.

Advantages of embodiments of the present invention include: Automation or assistance of eye docking in the treatment workflow enhances the alignment accuracy and also shortens the treatment time. Both will improve the diagnostic and treatment outcome. The shortened treatment time also contributes to patient comfort.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides an ophthalmic surgical laser system, which includes: a laser delivery head, including optics which define an optical axis for delivering a laser beam to an eye of a patient; an magnetic field sensing system, which includes a first, a second, a third and a fourth magnetic field sensors and a control device electrically coupled to the first through fourth sensors, wherein the first through fourth sensors are affixed on the laser delivery head and located in a plane perpendicular to the optical axis, wherein the first and second sensors have identical structures and are located at equal distances from the optical axis along a first line that passes through the optical axis, wherein the third and fourth sensors have identical structures and are located at equal distances from the optical axis along a second line that passes through the optical axis, and wherein the control device is configured to control each of the first through fourth sensors to measure a magnetic field generated by an external magnet, and based on the measured magnetic field signals by the first through fourth sensors, to determine whether or not the external magnet is located within a predetermined distance from the optical axis.

In another aspect, the present invention provides a patient interface device for use in ophthalmic surgery, which includes: a body having a round shape and defining a central area for accommodating an optical path of a laser beam; an annular flexible skirt located at a lower end of the body; and a ring shaped magnet disposed on the body, the magnet being centered on a rotational axis of the body.

In yet another aspect, the present invention provides a method for docking an ophthalmic surgical laser system to a patient's eye, the laser system including a laser delivery head which defines an optical axis for delivering a laser beam into the patient's eye, a mechanical structure configured to move the laser delivery head, and a magnetic field sensing system, the magnetic field sensing system including first to fourth magnetic field sensors and a control device, wherein the first through fourth sensors are affixed on the laser delivery head and located in a plane perpendicular to the optical axis, the first and second sensors have identical structures and are located at equal distances from the optical axis along a first line that passes through the optical axis, and the third and fourth sensors have identical structures and are located at equal distances from the optical axis along a second line that passes through the optical axis, the method including: (a) controlling each of the first through fourth sensors to measure a magnitude of a magnetic field generated by an external magnet; (b) based on the measured magnetic field magnitude by the first through fourth sensors, determining whether or not the external magnet is located within a predetermined distance from the optical axis; and (c) based on the measured magnetic field magnitude by the first through fourth sensors, controlling the mechanical structure to move the laser delivery head toward the external magnet.

It is to be understood that both the foregoing general description and the following detailed description are exem-

DETAILED DESCRIPTION OF PREFERRED EMBODIMENTS

Eye docking is a critical first step in many ophthalmic diagnostic and treatment procedures. Currently all known eye docking systems require manual manipulation of the instrumentation head (e.g. laser head) in three dimensions to align the instrumentation head to the PI piece that is installed on the eye. The manipulation is typically performed using joystick or other input devices, either real or virtual, with the aid of a video camera. The feedback to the surgeon is the image showing the eye and parts of the laser head, which requires manual interpretation. This alignment requires dexterity and careful attention by the surgeon. Inexperience can significantly prolong the overall treatment time and add to patient discomfort. In current procedures, the only registration automation occurs after the eye is docked in place, i.e., after the laser head is coupled to the PI and the optical imaging system within the laser head is able to acquire images of the eye through the PI.

Embodiments of the present invention provides a magnetic positioning system and related methods that aid automatic docking in the "mid-range" of the overall eye registration operation, i.e., after the laser head is brought to within, for example, approximately 1 foot (approximately 30 cm) of the PI piece that has been installed on the eye, and before the laser head is sufficiently aligned and close to the PI piece such that the optical imaging system within the laser head is able to acquire images of the eye through the PI. Embodiments of the invention provide for automatic detection of relative position of the laser head with respect to the PI piece when they are within the operating range of approximately 1-2 feet from each other; the relative position information is used to automatically, without operator intervention, move the laser head toward the PI piece until the laser head is within a sufficiently close distance to the PI piece in at least the transverse directions (directions perpendicular to the optical axis of the laser head), e.g. within a few mm, e.g., 3 mm. Position detection is accomplished using magnetic field sensing.

Figure 1:
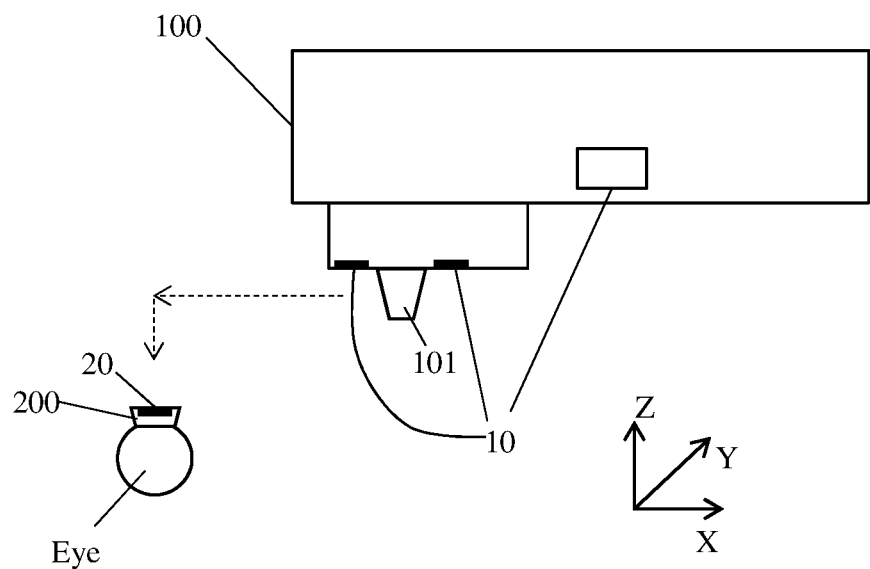
FIG. 1 schematically illustrates an ophthalmic surgical laser system incorporating a magnetic field sensing system for automatic or assisted eye docking according to an embodiment of the present invention.

More specifically, as schematically illustrated in FIG. 1, the magnetic positioning system includes one or more magnets 20 provided on the PI piece 200 that is mounted on the patient's eye, and a magnetic field sensing system 10 with multiple magnetic field sensors provided on the laser head 100 to detect the magnetic field generated by the magnet. The magnetic signals detected by the multiple magnetic field sensors are used to determine or estimate the 3D position of the magnet and to move the laser head toward the PI piece. The laser head 100 includes mechanical structures controlled by a controller to move the laser head in X, Y and Z directions. Note that the illustration in FIG. 1 is highly schematic and is not intended to represent the actual shape, size, proportion, or precise physical location of the various components.

Embodiments of the present invention are applicable to both a laser ophthalmic surgery system that employs a two-piece PI, where the magnet is provided on the PI piece that is installed on the eye, and to a laser ophthalmic surgery system that employs a single-piece PI, where the magnet is provided on the PI and the PI is installed on the eye before it is docked to the laser head. In the descriptions herein, for convenience, the PI piece that has the magnet provided on it is referred to as "the PI" 200 for both types of systems.

Preferably, the one or more magnets on the PI have their north and south poles oriented in the direction parallel to the central axis of the PI, which is expected to be oriented in the vertical (Z) direction during the eye docking operation.

The magnetic field sensing system located on the laser head includes multiple magnetic field sensors, each sensor detecting the X, Y and Z components (i.e. a vector) of the magnetic field at its location. The magnetic field sensing system also includes a control device (which may include hardware circuits, a processor with memory storing computer programs, or other types of circuitry) for processing the signals generated by the magnetic field sensors, as well as a power source. Any suitable magnetic field sensors may be used. The multiple sensors are located at fixed locations on the laser delivery head. For example, the laser head may have a bottom surface from which a cone shaped housing 101 (see FIG. 1) protrudes; the sensors may be mounted on the bottom surface around this housing. Based on the magnitude of the magnetic field detected by different sensors, the control device determines the relative location of the magnet with respect to the sensors, and accordingly controls the movement of the laser delivery head to center it relative to the PI for docking to the PI.

Figure 2:
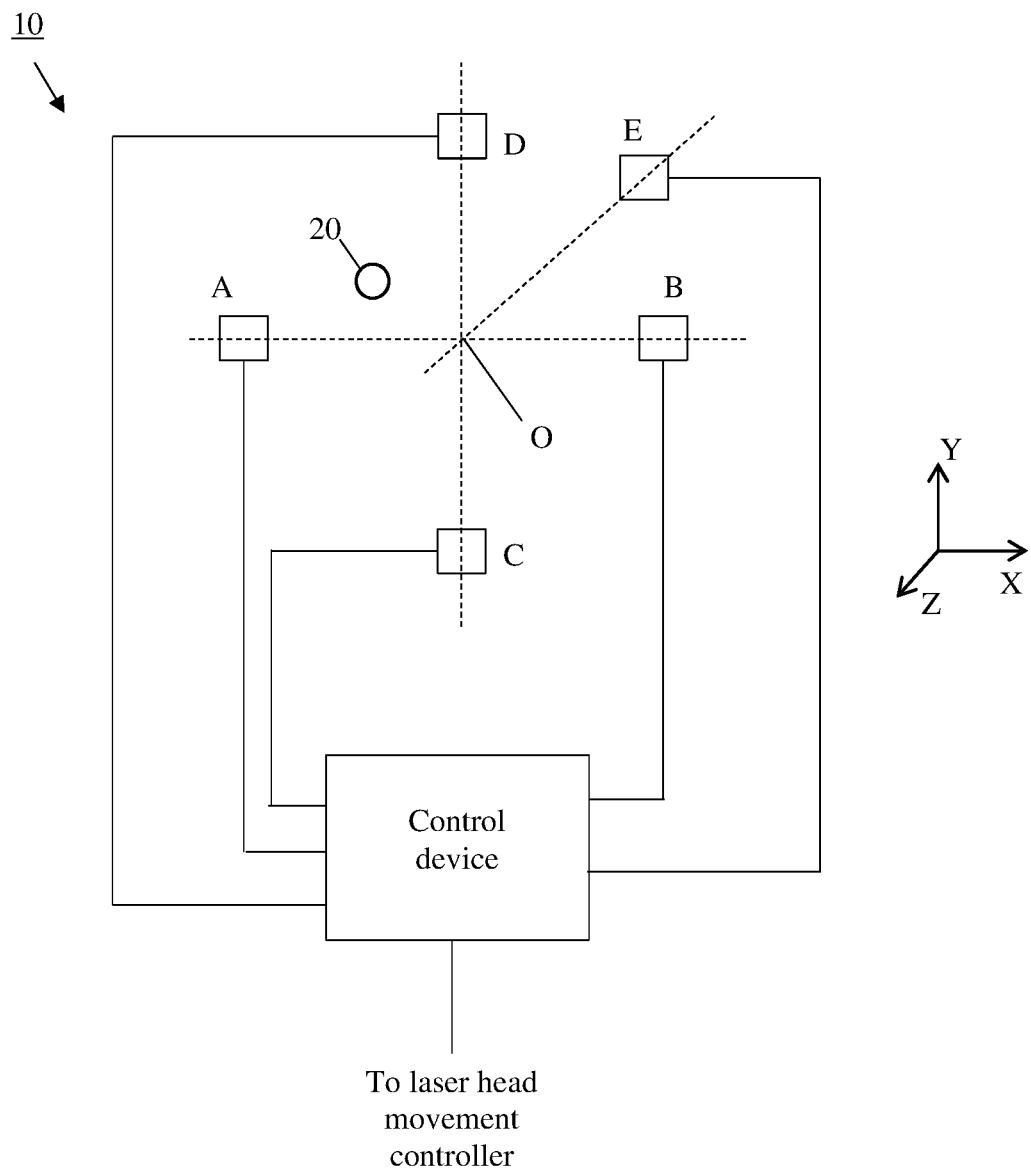
FIG. 2 schematically illustrates the structure of the magnetic field sensing system according to an embodiment of the present invention.

In one embodiment, schematically illustrated in FIG. 2, the magnetic field sensing system employs five magnetic field sensors A-E. Four of the sensors A, B, C and D are identical in structure and located in an X-Y plane (horizontal plane which is perpendicular to the optical axis of the laser head) at the same distance from a center position O in the −X, +X, −Y and +Y directions, respectively. The distance from the center may be in the range of 1 to 100 cm, preferably 5 to 20 cm, more preferably about 10 cm. As will be discussed later, other sensor configurations are possible. The fifth sensor E is located above or below the X-Y plane. For example, the fifth sensor E may be located within or on the housing 101 (see FIG. 1). The fifth sensor E is optional. The center position O is the intersection of the X-Y plane and the optical axis of the laser beam to be delivered to the eye, which also corresponds to the intended docking position of the PI; i.e., the PI is deemed to be correctly docked when the magnet is located at the position (0, 0, −z) in the X-Y-Z coordinate system, Z being the vertical direction and parallel to the optical axis of the laser head. FIG. 2 schematically shows the magnet 20 being at an off-centered position.

When the magnet is located between the sensors A and B in the X direction, the magnitudes of the magnetic field detected by sensors A and B are used by the control device to determine the position of the magnet along the X axis. Likewise, when the magnet is located between the sensors C and D in the Y direction, the magnitudes of the magnetic field detected by sensors C and D are used by the control device to determine the position of the magnet along the Y axis. The magnet is deemed to be centered in the X-Y directions when the magnitudes of the magnetic field detected by the sensors A and B are equal, and the magnitudes of the magnetic field detected by the sensors C and D are equal. The magnitude of the magnetic field detected by the fifth sensor E relative to the average magnitude of the in-plane sensors A to D is used by the control circuitry to determine the relative position of the magnet along the Z axis. The relative magnitude detected by the sensor E that corresponds to the correctly docked position of the PI may be established empirically.

Here, those skilled in the art would appreciate that when two quantities are said to be equal, what is meant is that their difference is less than a threshold which may depend on noise level in the signal and instrument limitations.

In addition to the magnetic field generated by the magnet on the PI, there exist naturally occurring background magnetic fields and magnetic field gradients, either static or time-varying. By using a plurality of sensors in the manner described above, such background magnetic signals are measured and compensated for.

As the goal of the magnetic positioning system is to accurately and precisely center the magnet at the center position O defined by the multiple sensors of the magnetic field sensing system, it is in fact not critical to precisely determine the position of the magnet when it is at an arbitrary off-centered position; what is important is to determine whether the magnet is precisely centered. As pointed out above, whether the magnet is centered can be determined by whether the magnitudes of the magnetic field detected by sensors A and B, and by sensors C and D, are respectively equal to each other. By using the multiple sensors A-D in the configuration described above, the precision of the position centering within a few mm or better can be achieved. In other words, the magnetic field sensing system is able to determine whether the magnet is located at within a few mm or less from the center position O defined by the multiple sensors (i.e. from the optical axis of the laser head).

Thus, when the magnet is at a location relatively far away from the center position, mm level of precision is not required; it is sufficient for the magnetic field sensing system to determine the approximate position of the PI or the approximate direction (in the X-Y plane) that the laser head needs to be moved in order to move it toward the PI. The magnetic positioning system is also able to estimate the approximate position of the PI when the PI is located outside of the square region bound by the four sensors A-D.

In some embodiments, the operating range of the magnetic positioning system, i.e. the farthest distance of the magnet from the center position O of the magnetic sensors such that the system can reliably operate to bring the laser head toward the PI, is approximately 1 foot (30 cm) or more. An operating range of 1 foot is sufficient for the purpose of automated docking, i.e., the surgeon only needs to manually move the laser head to within 1 foot from the PI.

During automated eye docking, the magnetic positioning system controls the movement of the laser head via a laser head movement controller. In a preferred embodiment, the laser head is initially position at a height above the PI, and controlled by the magnetic positioning system to automatically move in the horizontal (X-Y) plane first to center it above the PI, and then controlled to move in the vertical (Z) direction to lower it to dock with the PI. The magnetic positioning system may control the movement of the laser head using various modes, including continuous, stepwise, trial and error, etc., or combinations thereof. In a continuous mode, the laser head is controlled to move continuously in one direction in the X-Y plane, and the magnetic field sensing system continuously monitor the signals from the multiple sensors A-D to provide feedback signals to maintain or change the movement speed and/or direction. In a stepwise mode, the signals from the sensors A-D are measured and evaluated to estimate a horizontal direction of movement that will bring the laser head closer to the PI; the laser head is controlled to move in that direction by a certain amount (without continuous monitoring of the magnetic signals); and the signals from the sensors A-D are measured again and evaluated to determine the next step of movement. In a trial an error mode, which may be employed when the laser head is located a relatively far away from the PI, the initial movement may be in an arbitrary direction, and the magnetic signals are measured both before and after the initial movement to determine whether or not the laser head has been moved in the correct direction. In all of these modes or their combination, the movement stops when the laser head reaches the center position as determined based on the magnetic signals from the multiple sensors A-D.

After the laser head is centered above the eye, it is controlled to move downwards to dock with the PI, as schematically shown by the dashed-line arrows in FIG. 1. As mentioned earlier, the magnitude of the magnetic signal detected by the fifth sensor E relative to the average signal magnitude of the in-plane sensors A to D may be used to determine the relative position of the magnet along the Z axis, and control the downward movement of the laser head. Also as mentioned earlier, the fifth sensor E is optional. When the fifth sensor is not used, the final docking movement in the Z direction may be manually controlled, or controlled by other feedback systems.

In addition to the sensor configuration shown in FIG. 2 and described above, other sensor configurations may be used. For example, in one alternative configuration, sensors A and B are at equal distance from the center O, and sensors C and D are at equal distance from the center O, but the distance from sensor C (and D) to the center O is different from the distance from sensor A (and B) to the center O. In another alternative configuration, the second pair of sensors C and D are not located along the Y axis, but are located along a line in the X-Y plane that passes through the center O but is at a non-orthogonal angle with respect to the X axis. In yet another alternative configuration, sensors A and B have identical structures and sensors C and D have identical structures, but sensors C and D have a different structure than sensors A and B.

Some other alternative sensor configurations may use fewer or more than four in-plane sensors, such as three (e.g., forming an equal-sided triangle) or six (e.g., forming an equal-sided hexagon). Depending on the number and locations of the multiple sensors, position determination based on the relative signal magnitudes may be more complex than that using the configuration of FIG. 2. One method for position determination is to calibrate the system beforehand, by recording the relative signal magnitudes among the sensors at multiple known PI locations (e.g. a grid of locations). A lookup table (LUT) may be constructed, and then used to estimate the location of the PI and to move the laser head toward the PI.

Figure 3:
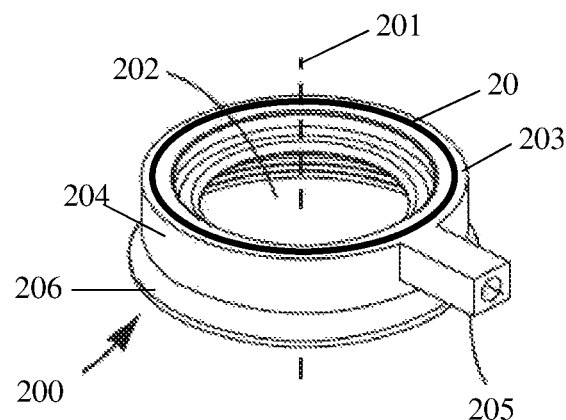
FIG. 3 schematically illustrates a patient interface incorporating a magnet according to an embodiment of the present invention.

As shown in FIG. 3, the one or more magnet 20 may be provided on the PI 200 at any suitable location or locations. The PI typically has a round shape, such as a ring, a truncated cone, etc. The magnet is preferably locate on the PI such that the shape of the magnetic field it generates is centered on the rotational axis 201 of the PI. As mentioned earlier, the north and south poles of the magnets are preferably oriented in the direction parallel to the rotational axis of the PI. Meanwhile, the one or more magnets should be positioned without obscuring a central area 202 of the PI that accommodates the optical path of the laser beam. Thus, one ring shaped magnet centered on the optical axis 201 may be used. Alternatively, multiple magnets may be used and distributed evenly in a circle around the optical axis. For example, one or more magnets 20 may be located on an upper rim 203 of the PI as shown in FIG. 3. FIG. 3 also illustrates a flexible skirt 206 located at the lower end of the PI 200, configured to contact the anterior surface of the patient's eye when the PI is mounted on the eye.

The inventors have constructed a test system using three magnetic field sensors and demonstrated that it can achieve position centering of the magnet within a few mm, with the centered position being about 8-10 cm from the sensors. The test system used a disc magnet having a diameter of about 10 mm and thickness of about 2 mm.

It is noted that the magnetic field vector in the area surrounding the PI is affected by both the translational position and the orientation angles (e.g. pitch and tilt) of the magnetic axis of the PI. In one embodiment, the positioning method adopts a simplifying assumption that the surgeon holds the PI so that its N-S magnetic axis remains approximately aligned with the optical axis of the laser head. It has been experimentally determined that in such a case, detecting only the scalar magnetic field strength is sufficient to accurately center the PI within a few mm. In this embodiment, while the sensors themselves are capable of measure the X, Y and Z components of the magnetic field vector separately, the components are combined to form a scalar magnitude which is used for positioning.

In the more general case that the PI, and hence its magnetic field, is allowed to significantly pitch or tilt away from the optical axis of the laser head, the centering position accuracy will be less than a few mm unless the control device uses all three (X, Y, Z) components of the magnetic field separately at each sensor position. This additional information enables the control device to estimate all degrees of freedom of the PI, e.g. the translational position in the X, Y, Z directions simultaneously with the pitch and tilt angles. With a known total magnetic field strength at the PI, that sensor data allows the vector magnitude of any external stray magnetic fields to be calculated as well. That enables accurate alignment of the PI in five degrees of freedom, namely X, Y, Z, pitch, and tilt, even in the presence of additional stray magnetic fields.

In addition to eye docking in ophthalmic procedures, the automated or assisted docking system according to embodiments of the present invention may be useful in any surgical or diagnostic instrumentation that requires alignment of the instrument to a specific body part, or other systems where one part is required to be physically aligned with another part.

It will be apparent to those skilled in the art that various modification and variations can be made in the automatic docking system using magnetic positioning and related method of the present invention without departing from the spirit or scope of the invention. Thus, it is intended that the present invention cover modifications and variations that come within the scope of the appended claims and their equivalents.

What is claimed is:

1. An ophthalmic surgical laser system comprising:
  a laser delivery head, including optics which define an optical axis for delivering a laser beam to an eye of a patient; and
  an magnetic field sensing system, which includes a first, a second, a third and a fourth magnetic field sensors and a control device electrically coupled to the first through fourth sensors,
  wherein the first through fourth sensors are affixed on the laser delivery head and located in a plane perpendicular to the optical axis, wherein the first and second sensors have identical structures and are located at equal distances from the optical axis along a first line that passes through the optical axis, wherein the third and fourth sensors have identical structures and are located at equal distances from the optical axis along a second line that passes through the optical axis, and
  wherein the control device is configured to control each of the first through fourth sensors to measure a magnetic field, and based on the measured magnetic field signals by the first through fourth sensors, to determine whether or not an external magnet that has generated the magnetic field is located within a predetermined distance from the optical axis.

2. The ophthalmic surgical laser system of claim 1, wherein the control device determines that the external magnet is located within the predetermined distance from the optical axis when the measured magnetic field by the first and second magnets are of equal magnitudes and when the measured magnetic field by the third and fourth magnets are of equal magnitudes.

3. The ophthalmic surgical laser system of claim 1, wherein the predetermined distance is 3 mm.

4. The ophthalmic surgical laser system of claim 1, wherein the first line and the second line are orthogonal to each other.

5. The ophthalmic surgical laser system of claim 4, wherein the first through fourth sensors have identical structures and are located at equal distances from the optical axis.

6. The ophthalmic surgical laser system of claim 1,
  wherein the magnetic field sensing system further includes a fifth magnetic field sensor located outside of the plane,
  wherein the control device is further configured to control the fifth sensor to measure the magnetic field, and
  wherein the control device is further configured to determine, based on the measured magnetic field magnitude by the first through fifth sensors, a relative position of the external magnet that generated the magnetic field in a direction along the optical axis.

7. The ophthalmic surgical laser system of claim 1, wherein the control device is configured to move the laser delivery head based on the measured magnetic field magnitudes by the first through fourth sensors.

8. The ophthalmic surgical laser system of claim 7, wherein the control device is configured to move the laser delivery head toward the external magnet.

9. The ophthalmic surgical laser system of claim 1, wherein the control device is configured to control each of the first through fourth sensors to measure a magnetic field vector generated by the external magnet, and based on the measured magnetic field vectors, to further determine a pitch and a tilt angle of the external magnet relative to the optical axis.

10. An ophthalmic surgical laser system comprising:
  a patient interface device which includes:
    a body having an annular shape and defining a central area for accommodating an optical path of a laser beam and a central axis within the central area;
    an annular skirt located at one end of the body; and a ring shaped magnet disposed on the body along a perimeter of the annular shape and around the central area, the magnet being centered on the central axis of the body;

a laser delivery head, including optics which define an optical axis for delivering a laser beam to an eye of a patient; and a magnetic field sensing system, which includes a first, a second, a third and a fourth magnetic field sensors and a control device electrically coupled to the first through fourth sensors, wherein the first through fourth sensors are affixed on the laser delivery head and located in a plane perpendicular to the optical axis, wherein the first and second sensors have identical structures and are located at equal distances from the optical axis along a first line that passes through the optical axis, wherein the third and fourth sensors have identical structures and are located at equal distances from the optical axis along a second line that passes through the optical axis, and wherein the magnet of the patient interface device is configured to generate a magnetic field, and wherein the control device is configured to control each of the first through fourth sensors to measure the magnetic field, and based on the measured magnetic field signals by the first through fourth sensors, to determine whether or not the magnet of the patient interface device is located within a predetermined distance from the optical axis.

11. A method for docking an ophthalmic surgical laser system to a patient's eye, the laser system comprising a laser delivery head which defines an optical axis for delivering a laser beam into the patient's eye, and a magnetic field sensing system, the magnetic field sensing system including first to fourth magnetic field sensors and a control device, wherein the first through fourth sensors are affixed on the laser delivery head and located in a plane perpendicular to the optical axis, the first and second sensors have identical structures and are located at equal distances from the optical axis along a first line that passes through the optical axis, and the third and fourth sensors have identical structures and are located at equal distances from the optical axis along a second line that passes through the optical axis, and wherein the control device is operatively coupled to the laser delivery head, the method comprising:

(a) installing a patient interface device on the patient's eye, the patient interface device including a magnet configured to generate a magnetic field;

(b) the control device controlling each of the first through fourth sensors to measure a magnitude of the magnetic field generated by the magnet of the patient interface device;

(c) based on the measured magnetic field magnitude by the first through fourth sensors, the control device determining whether or not the magnet of the patient interface device is located within a predetermined distance from the optical axis; and (d) based on the measured magnetic field magnitude by the first through fourth sensors, the control device moving the laser delivery head toward the magnet of the patient interface device.

12. The method of claim 11, wherein step (c) includes: the control device determining that the magnet of the patient interface device is located within the predetermined distance from the optical axis when the measured magnetic field magnitudes by the first and second sensors are equal and when the measured magnetic field magnitudes by the third and fourth sensors are equal.

13. The method of claim 11, wherein the predetermined distance is 3 mm.

14. The method of claim 11, wherein the magnetic field sensing system further includes a fifth magnetic field sensor located outside of the plane, wherein the method further comprises:

the control device controlling the fifth sensor to measure a magnitude of the magnetic field generated by the magnet of the patient interface device; and based on the measured magnetic field magnitude by the first through fifth sensors, the control device determining a relative position of the magnet of the patient interface device in a direction along the optical axis.

15. The method of claim 11, wherein step (b) further includes the control device controlling each of the first through fourth sensors to measure three components of a magnetic field vector generated by the magnet of the patient interface device;

wherein step (c) includes, based on the measured magnetic field vector components by the first through fourth sensors, the control device determining whether or not the magnet of the patient interface device is located within a predetermined distance from the optical axis; and wherein step (d) includes, based on the measured magnetic field vector components by the first through fourth sensors, the control device moving the laser delivery head toward the magnet of the patient interface device.

* * * * *